United States Patent
Buschmann et al.

(10) Patent No.: US 8,168,679 B2
(45) Date of Patent: May 1, 2012

(54) SALTS OF TRAMADOL AND NAPROXEN AND THEIR CRYSTAL FORMS IN THE TREATMENT OF PAIN

(75) Inventors: Helmut Heinrich Buschmann, Barcelona (ES); Antoni Torrens-Jover, Barcelona (ES); Josep Mas-Prio, Barcelona (ES); Jordi Benet-Buchholz, Altafulla (ES); Lluis Sola-Carandell, Tarragona (ES); Jordi Carles Ceron-Bertran, Tarragona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 12/672,416

(22) PCT Filed: Jul. 31, 2008

(86) PCT No.: PCT/EP2008/006319
§ 371 (c)(1),
(2), (4) Date: Mar. 12, 2010

(87) PCT Pub. No.: WO2009/018959
PCT Pub. Date: Feb. 12, 2009

(65) Prior Publication Data
US 2010/0227927 A1    Sep. 9, 2010

(30) Foreign Application Priority Data
Aug. 7, 2007  (EP) .................................. 07384033

(51) Int. Cl.
*A01N 37/12*  (2006.01)
*A01N 37/44*  (2006.01)
*A01N 37/30*  (2006.01)
*A61K 31/195* (2006.01)
*A61K 9/22*   (2006.01)
*A61K 31/205* (2006.01)
*C07C 62/00*  (2006.01)
*C07C 65/00*  (2006.01)

(52) U.S. Cl. ......... 514/567; 562/466; 424/468; 514/554

(58) Field of Classification Search ........................ None
See application file for complete search history.

(56) References Cited

U.S. PATENT DOCUMENTS

| 2003/0044464 A1 | 3/2003 | Ziegler et al. |
| 2004/0076669 A1 | 4/2004 | Bartholomaus et al. |

(Continued)

FOREIGN PATENT DOCUMENTS

| DE | 3623193 A1 | 1/1988 |

(Continued)

OTHER PUBLICATIONS

Evans, G. R. et al; "Development of Highly Efficient Resolutions of Racemic Tramadol Using Mandelic Acid," Organic Process Research and Development, 2002, vol. 6, pp. 729-737.

(Continued)

*Primary Examiner* — Daniel Sullivan
*Assistant Examiner* — Jennifer C Sawyer
(74) *Attorney, Agent, or Firm* — Heslin Rothenberg Farley & Mesiti P.C.

(57) ABSTRACT

The present invention concerns salts of Tramadol and Naproxen and their crystalline forms, and compositions thereof, for the treatment of pain, as well as their process for preparation.

4 Claims, 12 Drawing Sheets

U.S. PATENT DOCUMENTS

Figure 1:
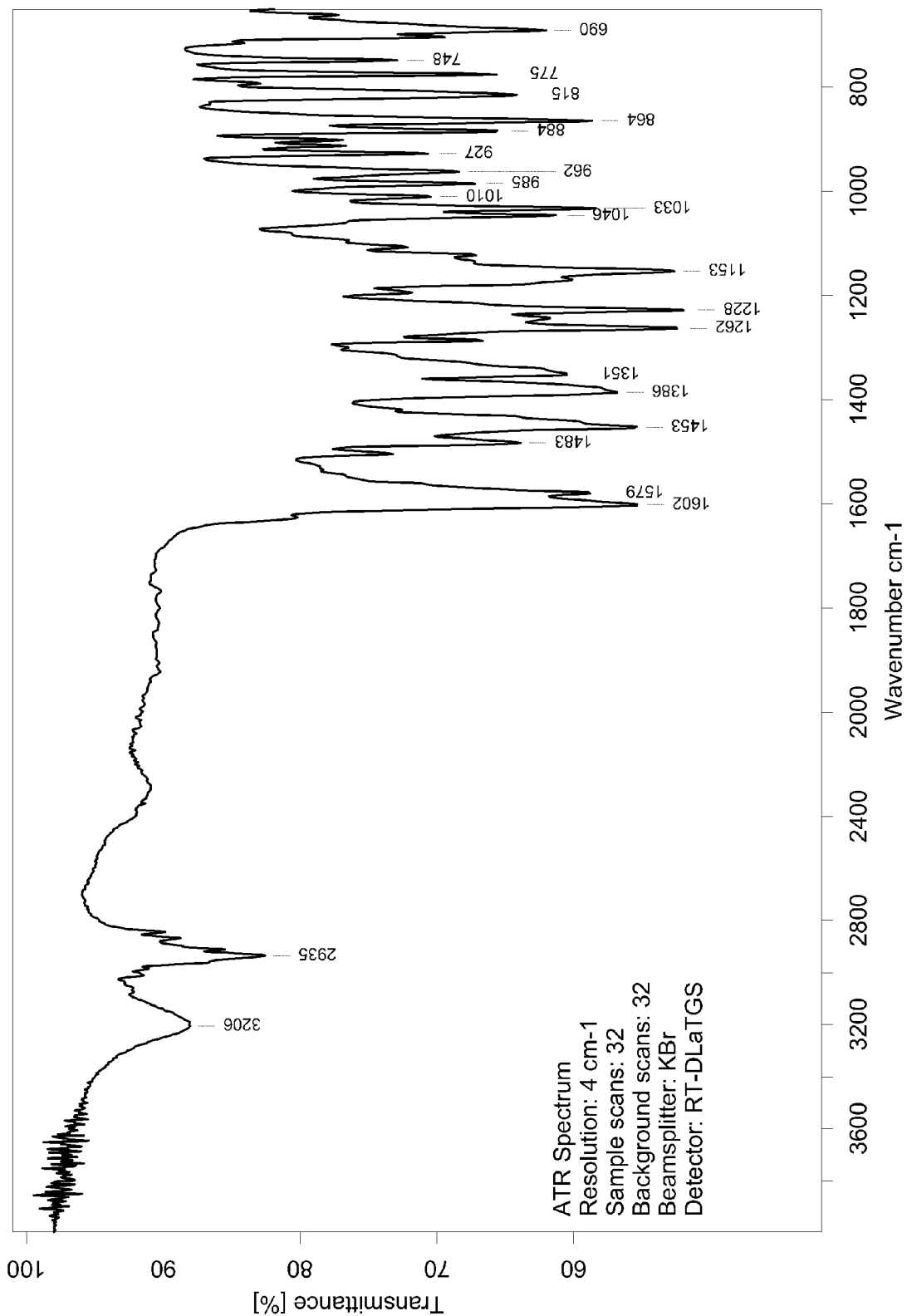

2005/0203115 A1    9/2005  Sancilio et al.
2006/0003428 A1*   1/2006  Tsai .......................... 435/135

FOREIGN PATENT DOCUMENTS

| EP | 0546676 A | 6/1993 |
| WO | 01/15667 A | 3/2001 |
| WO | 02/066025 A | 8/2002 |
| WO | 2004/022567 A | 3/2004 |

OTHER PUBLICATIONS

Pitre, D. et al; "Optical Resolution of I-amino-2,3-propanediol," Archiv der Pharmazie, 1986, vol. 319, No. 3, pp. 193-195.

International Search Report and Written Opinion for PCT/EP2008/006319 dated Oct. 8, 2008.

* cited by examiner

SALTS OF TRAMADOL AND NAPROXEN AND THEIR CRYSTAL FORMS IN THE TREATMENT OF PAIN

CROSS REFERENCE TO RELATED APPLICATIONS

This application is a U.S. National Phase filing under 35 U.S.C. §371 of International Application PCT/EP2008/006319, filed Jul. 31, 2008, and published as WO 2009/018959 on Feb. 19, 2009. PCT/EP2008/006319 claimed benefit of priority from European Patent Application No. EP 07384033.2, filed Aug. 7, 2007. The entire contents of each of the prior applications are incorporated herein by reference.

The present invention relates to salts of Tramadol and Naproxen, their crystal form, processes for preparing the same, and their use as medicaments, more particularly for the treatment of pain.

Pain is a complex response that has been functionally categorized into sensory, autonomic, motor, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus.

In general, pain conditions can be divided into chronic and acute. Chronic pain includes neuropathic pain and chronic inflammatory pain, for example arthritis, or pain of unknown origin, as fibromyalgia. Acute pain usually follows non-neural tissue injury, for example tissue damage from surgery or inflammation, or migraine.

There are many drugs that are known to be useful in the treatment or management of pain.

Opioids are frequently used as analgesics in pain. Derivatives of morphine are indicated for the treatment of moderate to acute pain in human. The analgesic effect is obtained through their action on morphinic receptors, preferably the μ receptors. Among these derivatives of morphine, may be mentioned morphine, codeine, pethidine, dextropropoxyphenemethadone, lenefopam.

One of the morphinic derivatives that have shown very good results when orally administrated, and which is now marketed, is Tramadol, also available as a physiologically acceptable salt, particularly as a chlorhydrate. Tramadol, whose chemical name is 2-(dimethylaminomethyl)-1-(3-methoxyphenyl)cyclohexanol, has the following formula:

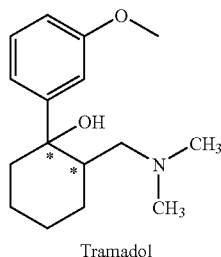

Tramadol

This structure shows two different chiral centers and thus may exist into different diastereoisomers among which the tramadol is the cis-diastereisomer: (1R, 2R), or (1S, 2S) both also known as (+)-tramadol ans (−)-tramadol, and both of which contribute in different ways to its activity.

From the art it appears that this compound is neither fully opioid-like, nor non-opioid-like. Some studies have demonstrate that tramadol is an opioid agonist, whereas clinical experience indicates that it lacks many of the typical side effects of opioids agonist, for example respiratory depression, constipation or tolerance.

Due to their drawbacks, opioids as analgesics to treat pain cannot always be given repeatedly or at higher doses. For reviewing side effects of opioids one can mention J. Jaffe in "Goodman and Gilman's, The Pharmacological Basis of Therapeutics", 8th edition; Gilman et al.; Pergamon Press, New York, 1990, Chapter 22, pages 522-573.

Consequently it has been proposed to combine opioids with other drugs that are not opioid analgesic agents, in order to lower the amount of opioids needed to produce an equivalent degree of analgesia. Among these combinations, the association of tramadol with nonsteroidal anti-inflammatory drugs (NSAIDs) has been reported to be of particular interest (EP-0 546 676).

One interesting NSAIDs to be combined with tramadol is the marketed drug naproxen, whose chemical name is 2(S)-(6-methoxy-2-naphtyl)propionic acid, and which is also described as a physiologically acceptable salt. This compound will be referred also as (S)-Naproxen.

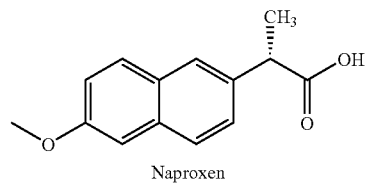

Naproxen

This compound exhibit a chiral center and thus may also exist as 2-(R)-(6-methoxy-2-naphtyl)propionic acid, also referred in the following as (R)-Naproxen.

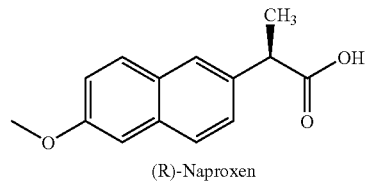

(R)-Naproxen

Different formulations have been designed to combine these two active principles, and due to its particular interest, it remains necessary to make new forms of this association available.

The applicant has now found that tramadol, especially the (R,R)-tramadol and the (S,S)-tramadol, having the opioid activity, and naproxen, especially (S)-naproxen and (R)-naproxen can be combined to form of a mixed-salt.

Generally each active principle forming part of the above mentioned salts according to the present invention has its own disadvantage when used alone or in the form of a known salt from the art.

Thus tramadol hydrochloride, despite the drawbacks described previously for the opioids, further display a highly bitter taste, which makes the drug often difficult to swallow and lowers patient compliance.

As far as naproxen is concerned, several salts have been already described. Nevertheless some of them are difficult to formulate, and basic counter cation is of no pharmaceutical value in itself, only adding molecular weight thus increasing the overall size of the pharmaceutical formulation without increasing the dosage.

Still there is a clear need for new salts of tramadol or naproxen either:
being active in pain or even more active when compared to tramadol base or hydrochloride salt or
being easily obtainable, or
being easily cristalised, allowing more flexibility in formulating, or
being highly soluble, especially if compared to tramadol or naproxen salts already known, allowing better dissolution rates, especially if dissolving in an aqueous physiological medium, or
having as acidic partner of the tramadol a molecule having a beneficial pharmacological effect in itself, thus allowing for a highly efficient dose/weight relation of the active principle; or
having as basic partner of the naproxen a molecule having a beneficial pharmacological effect in itself, thus allowing for a highly efficient dose/weight relation of the active principle.

Preferably, the new salt should combine more than one, and most preferably all of these advantages.

Thus the object of the present invention is the tramadol-naproxene salt of formula:

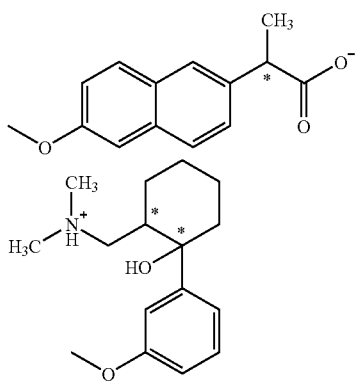

According to a preferred embodiment, the invention concerns the (R,R)-Tramadol-(S)-naproxene salt of formula:

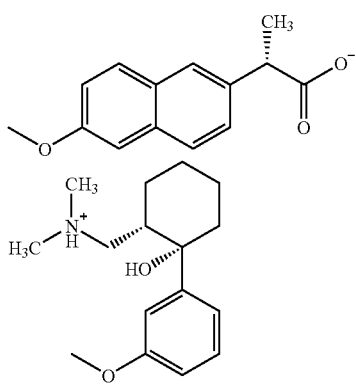

This association of the two active principles into the same salt exhibits several advantages. Being linked as ion and counter-ion, they behave as a single chemical entity, thus facilitating the treatments, formulation, dosage . . . .

The mixed salt according to the invention is not only surprisingly easily formed and crystallised it also considerably improves the solubility of naproxen. Also this association of the two active principles into the same salt exhibits several further advantages. Both tramadol and naproxen being active analgesics, these mixed salts are highly useful in the treatment of pain, especially also not losing any activity/weight by the addition of pharmacologically useless counter-ions. In addition the two active principles are complementing each other in the treatment especially of pain, but possibly also of various other diseases or symptoms. Also the individual dose of the opioid tramadol may be lowered, thus allowing a more frequent treatment, still with an equivalent degree of analgesia. Further, the combination of the two active principles into one unique species advantageously removes the bitter taste of the tramadol hydrochloride, which makes oral administration to a patient much easier. Thus, the mixed salts according to the invention do combine a high number of advantages over the state of the art.

Another embodiment of the invention concerns the salt of (R,R)-Tramadol-(R)-naproxene.

In a further embodiment the salt according to the present invention is the (S,S)-Tramadol-(R)-naproxene salt.

In a another embodiment, the present invention concerns the (S,S)-Tramadol-(S)-naproxene salt.

In still another embodiment, the present invention concerns the (R,R/S,S)-Tramadol-(R/S)-naproxene salt.

The present invention encompasses the above mentioned salts in an amorphous form as well as in crystalline form, and also the different polymorphs thereof.

The Applicant has further demonstrated the possibility to crystallise the salts according to the present invention. By that way the physico-chemical properties are improved. The formulation of the association is even easier with a solid to manipulate and an enhanced stability. The solubility, en particular the solubility of the naproxen salt is also greatly augmented.

Another advantage is that the combination of the two active principles into one unique species also allow for a better Pharmacokinetic/Pharmacodynamic (PKPD) including also a better penetration of the blood-brain barrier, which helps in the treatment of pain.

Thus a further object of the present invention is the crystalline form of tramadol-naproxene salts mentioned above.

In most embodiments in which the salts of tramadol are used (e.g. for the treatment of pain wtc.) these salts would be formulated into a convenient pharmaceutical formulation or a medicament. Accordingly a desirable advantage of a tramadol salt, especially if crystallized, would be the improvement of pharmaceutical properties and features, especially when compared to the free base or tramadol hydrochloride. Thus, the tramadol salt according to the invention, and especially the crystalline forms, should desirably show at least one, preferably more, of the following features:
to have a very small particle size, e.g. from 300 μm or lower; or
to be and/or remain essentially free of agglomerates; or
to be less or not very hygroscopic; or
to allow by selection of the counter-ion of the tramadol to help in formulating controlled release or immediate release formulations; or
to have a high chemical stability; or
if given to a patient
to decrease the inter- and intra-subject variability in blood levels; or
to show a good absorption rate (e.g. increases in plasma levels or AUC); or to show a high maximum plasma concentration (e.g. $C_{max}$); or to show decreased time to peak drug concentrations in plasma ($t_{max}$); or to show changes in half life of the compound ($t_{1/2}$), in whichever direction this change is preferably directed.

A further preferred object of the invention is a crystalline form of (R,R)-tramadol-(S)-naproxene salt.

More particularly, the invention concerns (R,R)-tramadol-(S)-naproxene salt or a crystalline form of (R,R)-tramadol-(S)-naproxene salt, characterized in that it shows a Fourier Transform Infra Red spectrum with absorption bands at 3206, 2935, 1602, 1579, 1483, 1453, 1386, 1351, 1263, 1228, 1153, 1046, 1033, 1010, 985, 962, 927, 884, 815, 775, 748 and 690 cm$^{-1}$ (see FIG. 1).

The invention also encompass (R,R)-tramadol-(S)-naproxene salt or a crystalline form of (R,R)-tramadol-(S)-naproxene salt for which the $^1$H NMR spectrum (see FIG. 2), in D4-methanol at 400 MHz shows peaks at 1.40-1.93 (m, 8H), 1.50 (d, J=7 Hz, 3H), 2.12 (m, 1H), 2.44 (dd, J=2 Hz, J=13 Hz, 1H), 2.46 (s, 6H), 2.79 (dd, J=9 Hz, J=13 Hz, 1H), 3.73 (q, J=7 Hz, 1H), 3.80 (s, 3H), 3.89 (s, 3H), 6.81 (dd, J=2 Hz, J=8 Hz, 1H), 7.00-7.11 (m, 3H), 7.18 (d, J=2 Hz, 1H), 7.27 (t, J=8 Hz, 1H), 7.48 (dd, J=2 Hz, J=8 Hz, 1H), 7.66-7.72 (m, 3H).

The (R,R)-tramadol-(S)-naproxene salt of the invention has a Specific rotation $[\alpha]_D^{26}$=+18.6° (c=1.00, MeOH).

Figure 3:
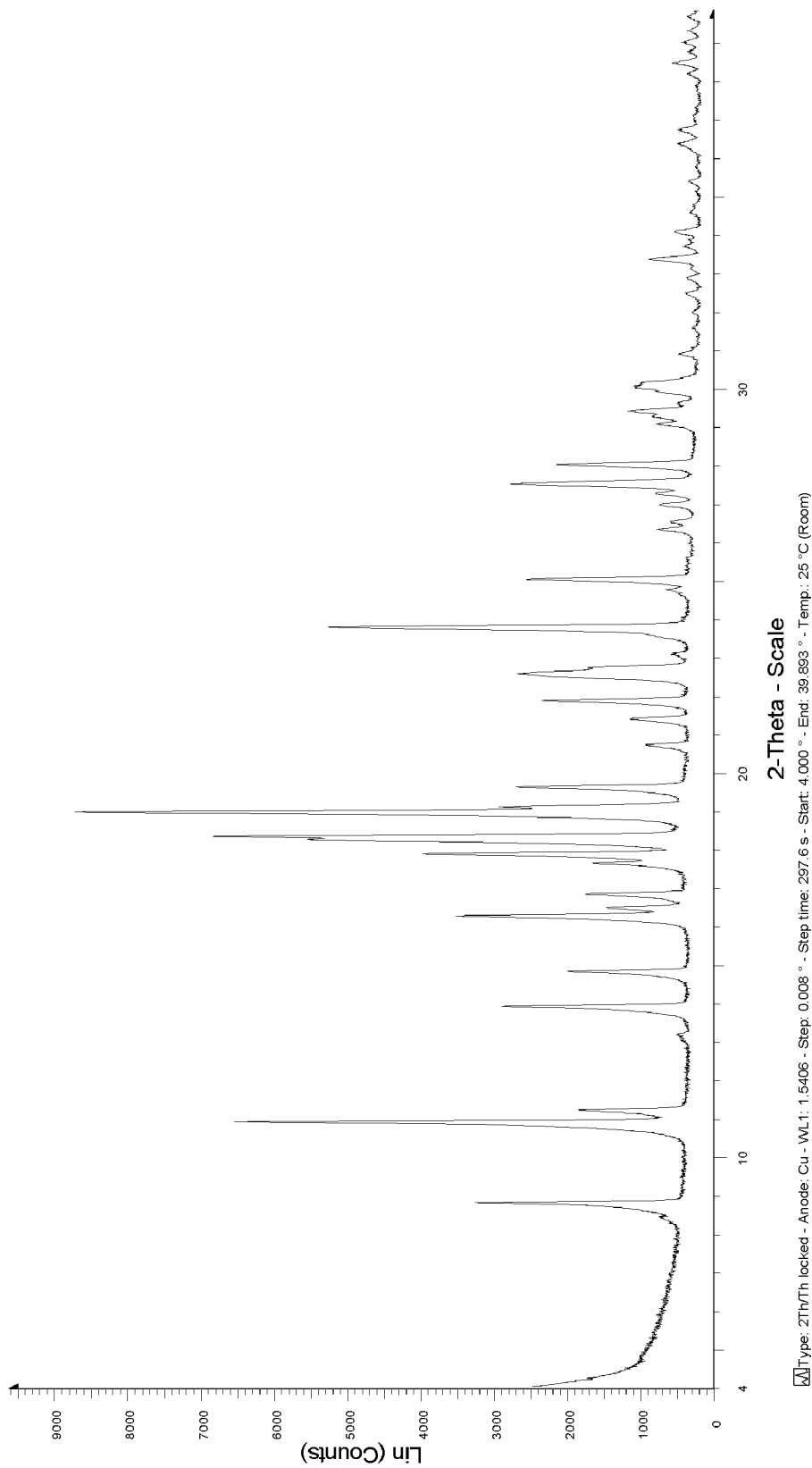

In another embodiment, the invention concerns a crystalline form of (R,R)-tramadol-(S)-naproxene salt, characterized in that it shows a X-Ray powder diffraction pattern as disclosed in FIG. 3, with the following peaks:

TABLE 1

List of selected peaks obtained by powder X-Ray diffraction of the salt.

| d-Value (Å) | Angle (2-Theta)[1] | Relative Intensity % |
|---|---|---|
| 10.06097 | 8.782 | 33.5 |
| 8.11136 | 10.899 | 73.4 |
| 7.89107 | 11.204 | 17.7 |
| 6.71252 | 13.179 | 2.0 |
| 6.36201 | 13.909 | 30.4 |
| 5.96828 | 14.831 | 19.8 |
| 5.44203 | 16.275 | 38.0 |
| 5.37442 | 16.481 | 13.3 |
| 5.25780 | 16.849 | 17.0 |
| 5.02147 | 17.648 | 15.8 |
| 4.95258 | 17.896 | 43.4 |
| 4.85099 | 18.274 | 62.2 |
| 4.83229 | 18.345 | 77.5 |
| 4.67202 | 18.980 | 100.0 |
| 4.63922 | 19.115 | 31.1 |
| 4.51720 | 19.637 | 28.4 |
| 4.27993 | 20.737 | 7.5 |
| 4.14654 | 21.412 | 10.1 |
| 4.05593 | 21.896 | 24.4 |
| 3.93014 | 22.606 | 28.5 |
| 3.90666 | 22.744 | 17.1 |
| 3.84436 | 23.117 | 3.1 |
| 3.73331 | 23.815 | 59.3 |
| 3.58933 | 24.785 | 4.5 |
| 3.54954 | 25.067 | 27.2 |
| 3.37803 | 26.362 | 6.1 |
| 3.35447 | 26.551 | 4.0 |
| 3.29816 | 27.013 | 5.9 |
| 3.26483 | 27.294 | 6.5 |
| 3.23509 | 27.550 | 30.1 |
| 3.17870 | 28.048 | 22.7 |
| 3.06515 | 29.110 | 6.7 |

[1]The 2-Theta values were obtained using cupper radiation (Cu$_{K\alpha}$ 1.54060 Å)

In another embodiment, the present invention concerns a crystalline form of (R,R)-tramadol-(S)-naproxene salt, characterized in that it crystallizes as a monoclinic cell with the following main characteristics:

Monoclinic chiral space group: P2$_1$
Volume: 1321.01(12) (Å$^3$)
Density: 1.241 Mg/m$^3$
Unit cell dimensions:
a=10.073(5) Å
b=12.487(6) Å
c=10.630(6) Å
α angle of 90°
β angle of 98.91(3)°.
γ angle of 90°
Absolute structure parameter: 0.02(0.13)

Figure 4:
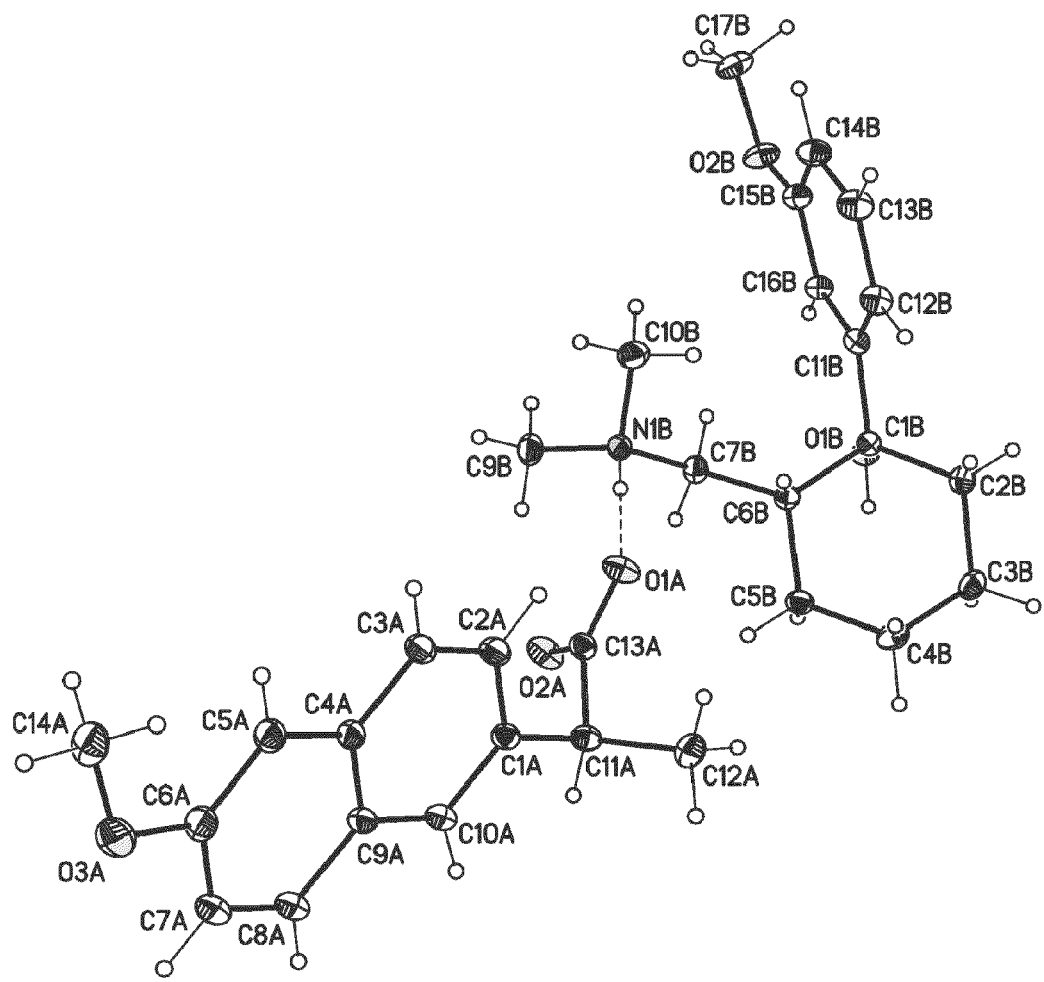

The spatial structure of the crystalline salt according to the invention is represented in FIG. 4.

Figure 5:
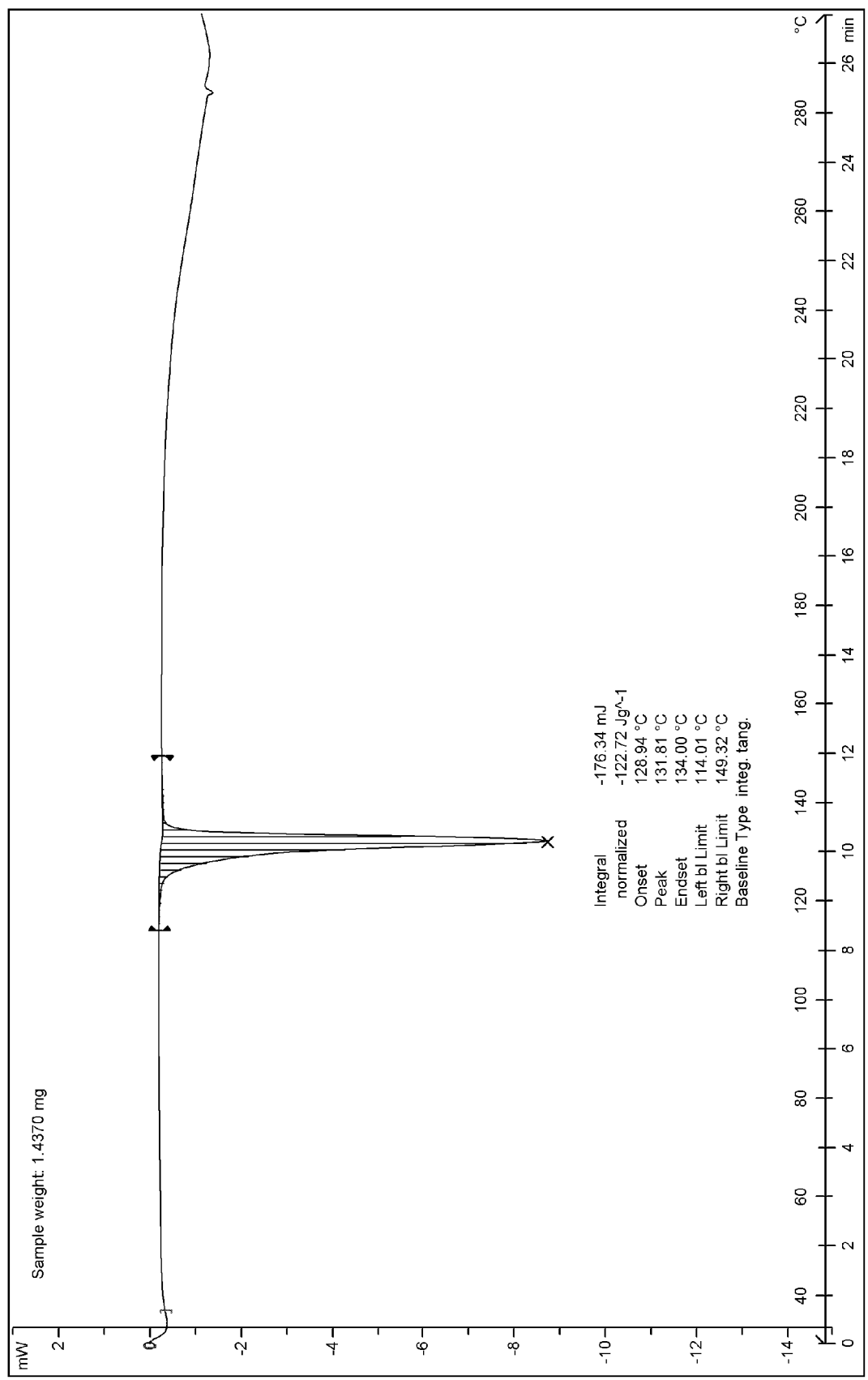

The crystalline form of (R,R)-tramadol-(S)-naproxene salt according to the present invention is characterized in that the endothermic sharp peak corresponding to the melting point has an onset at 129° C., measured by DSC analysis (10° C./min), see FIG. 5.

Figure 6:
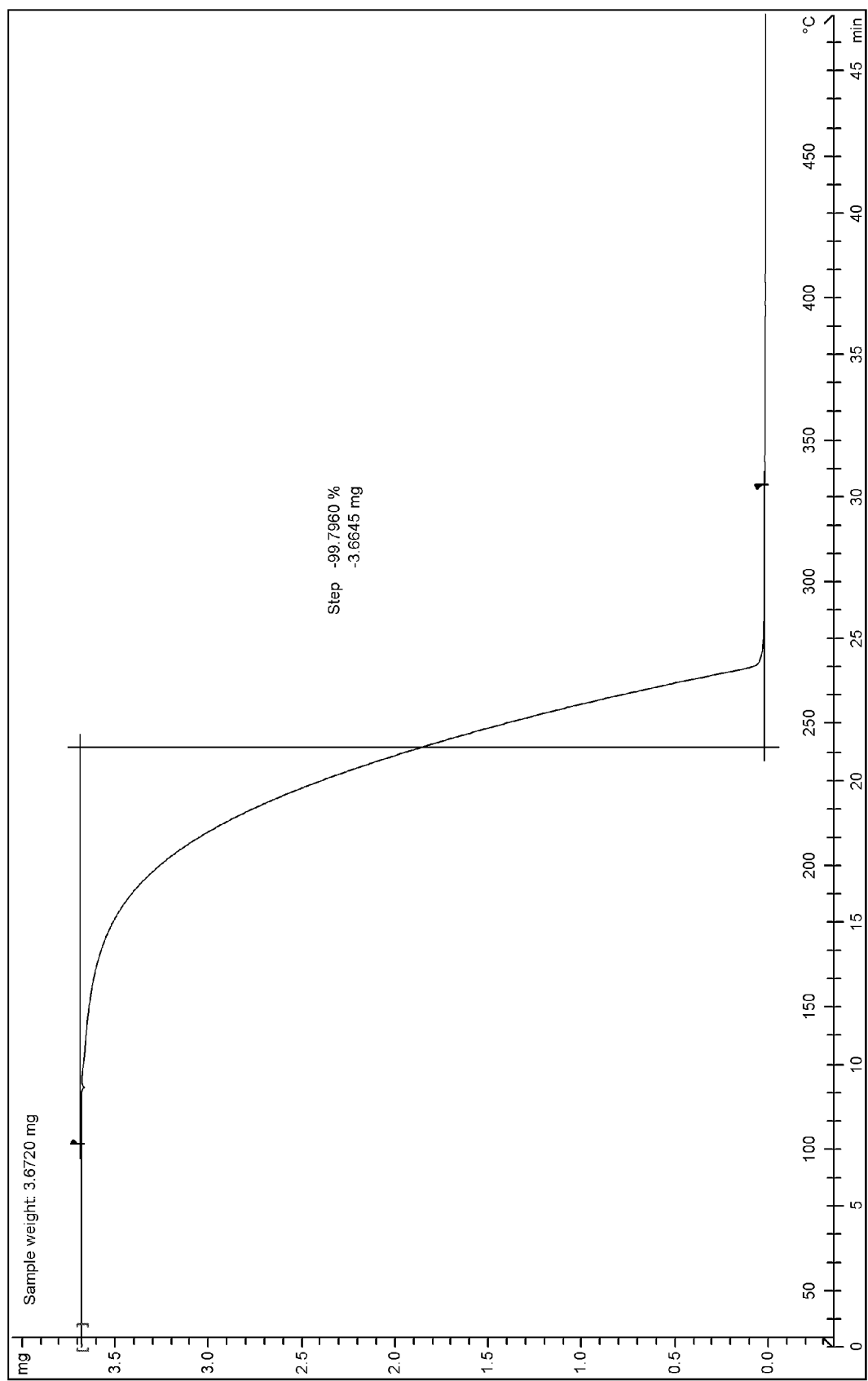

The TG analysis of the crystalline form according to the invention shows no weight loss at temperatures lower than the melting point (see FIG. 6).

A further preferred object of the invention is a crystalline form of (S,S)-tramadol-(R)-naproxene salt.

Figure 7:
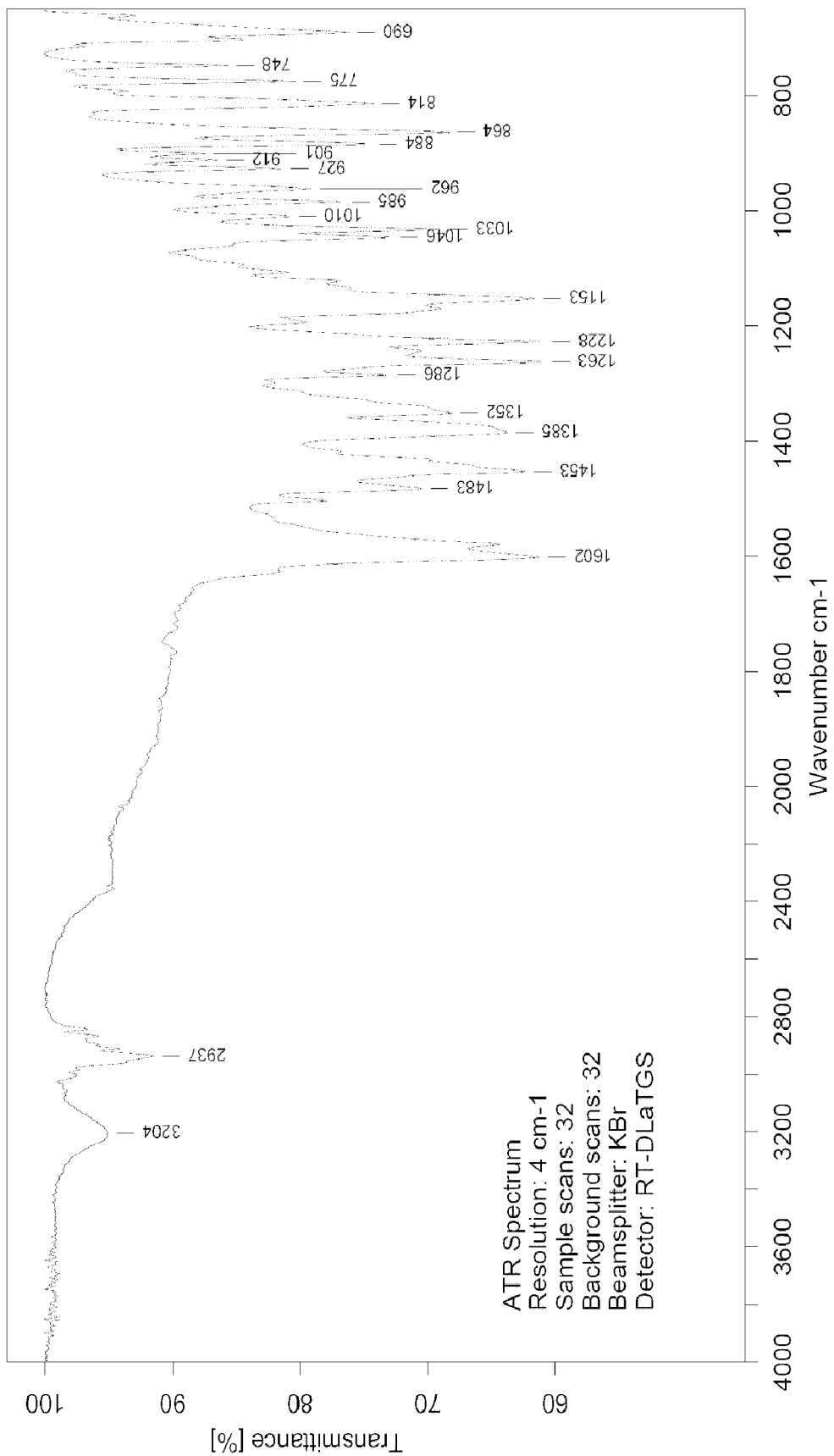

More particularly, the invention concerns (S,S)-tramadol-(R)-naproxene salt or a crystalline form of (S,S)-tramadol-(R)-naproxene salt, characterized in that it shows a Fourier Transform Infra Red spectrum with absorption bands at 3204, 2937, 1602, 1483, 1453, 1385 and 1352 cm$^{-1}$, 1263, 1228, 1153, 1046, 1033, 1010, 985, 962, 927, 884, 815, 775, 748 and 690 cm$^{-1}$ (see FIG. 7).

The invention also encompass (S,S)-tramadol-(R)-naproxene salt or a crystalline form of (S,S)-tramadol-(R)-naproxene salt for which the $^1$H NMR spectrum (see FIG. 8), in D4-methanol at 400 MHz shows peaks at 1.44-1.93 (m, 8H), 1.50 (d, J=7 Hz, 3H), 2.12 (m, 1H), 2.43 (dd, J=2 Hz, J=13 Hz, 1H), 2.47 (s, 6H), 2.79 (dd, J=9 Hz, J=13 Hz, 1H), 3.74 (q, J=7 Hz, 1H), 3.80 (s, 3H), 3.89 (s, 3H), 6.81 (ddd, J=1 Hz, J=3 Hz, J=8 Hz, 1H), 7.04 (d, J=7 Hz, 2H), 7.08 (dd, J=2 Hz, J=9 Hz, 1H), 7.18 (d, J=2 Hz, 1H), 7.28 (t, J=8 Hz, 1H), 7.48 (dd, J=2 Hz, J=9 Hz, 1H), 7.66-7.71 (m, 3H).

The (S,S)-tramadol-(R)-naproxene salt of the invention has a Specific rotation $[\alpha]_D^{26}$=−19° (c=1.00, MeOH).

Figure 9:
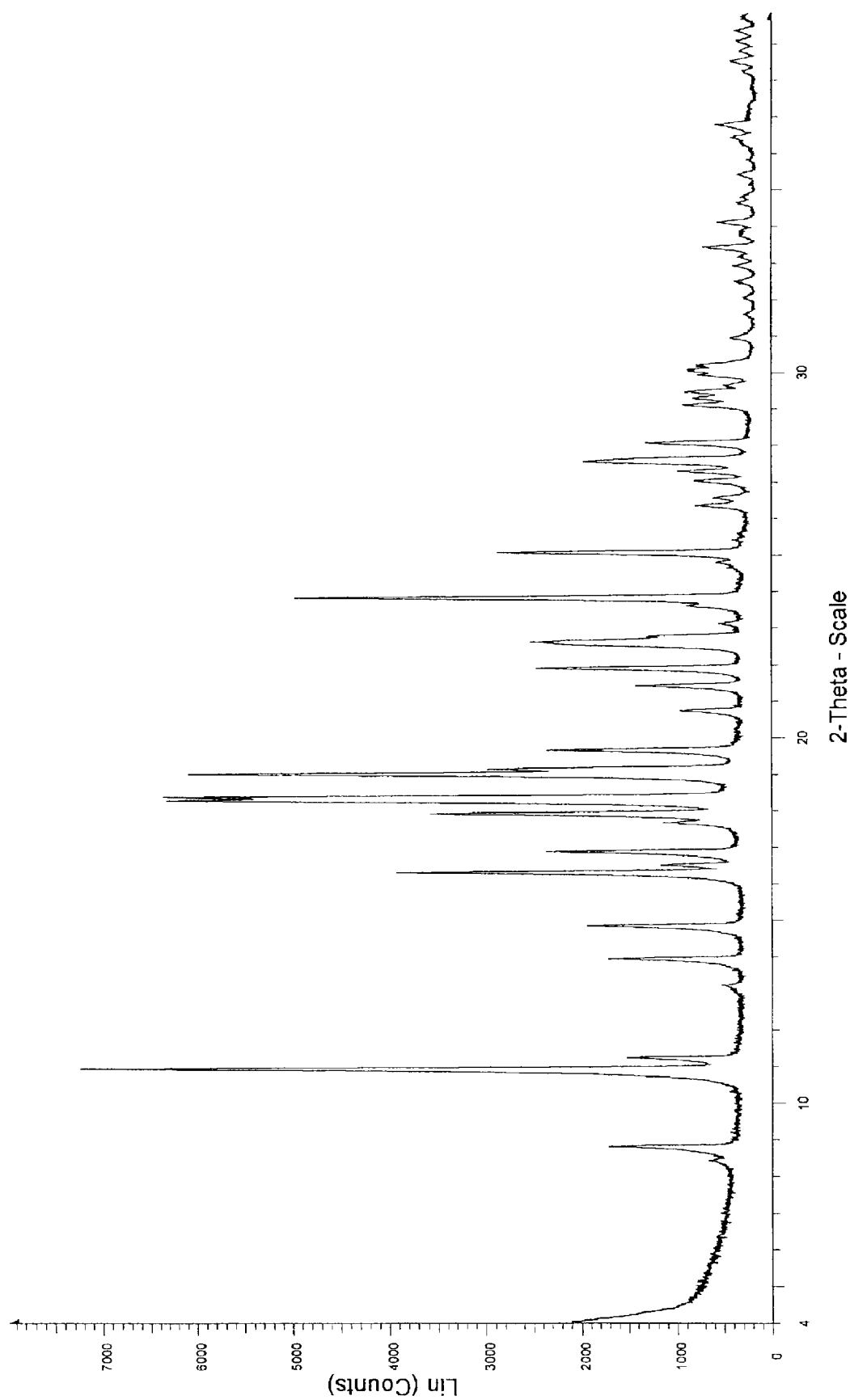

In another embodiment, the invention concerns a crystalline form of (S,S)-tramadol-(R)-naproxene salt, characterized in that it shows a X-Ray powder diffraction pattern as disclosed in FIG. 9, with the following peaks:

TABLE 2

List of selected peaks obtained by powder X-Ray diffraction of the salt.

| d-Value (Å) | Angle (2-Theta)[1] | Relative Intensity % |
|---|---|---|
| 10.51929 | 8.399 | 4.0 |
| 10.05203 | 8.790 | 20.4 |
| 8.10639 | 10.905 | 100.0 |
| 7.88393 | 11.214 | 18.1 |
| 6.70564 | 13.193 | 2.5 |
| 6.35529 | 13.923 | 21.3 |
| 5.96969 | 14.828 | 24.8 |
| 5.43768 | 16.288 | 54.6 |
| 5.36890 | 16.498 | 12.6 |
| 5.25441 | 16.860 | 30.7 |
| 5.01858 | 17.658 | 11.9 |
| 4.94826 | 17.911 | 49.0 |
| 4.85049 | 18.276 | 90.8 |
| 4.82500 | 18.373 | 91.7 |
| 4.66904 | 18.992 | 87.4 |

TABLE 2-continued

List of selected peaks obtained by powder X-Ray diffraction of the salt.

| d-Value (Å) | Angle (2-Theta)[1] | Relative Intensity % |
|---|---|---|
| 4.63369 | 19.138 | 40.1 |
| 4.51332 | 19.654 | 30.6 |
| 4.28014 | 20.736 | 9.8 |
| 4.14544 | 21.418 | 16.5 |
| 4.05596 | 21.896 | 32.4 |
| 3.92892 | 22.613 | 33.4 |
| 3.90111 | 22.777 | 14.9 |
| 3.84324 | 23.124 | 3.2 |
| 3.76577 | 23.607 | 8.7 |
| 3.73089 | 23.831 | 70.9 |
| 3.58693 | 24.802 | 4.2 |
| 3.54871 | 25.073 | 39.3 |
| 3.37817 | 26.361 | 8.2 |
| 3.35206 | 26.570 | 5.0 |
| 3.29589 | 27.032 | 8.3 |
| 3.26453 | 27.297 | 11.0 |
| 3.23193 | 27.577 | 26.3 |

[1]The 2-Theta values were obtained using cupper radiation ($Cu_{K\alpha}$ 1.54060 Å)

Figure 10:
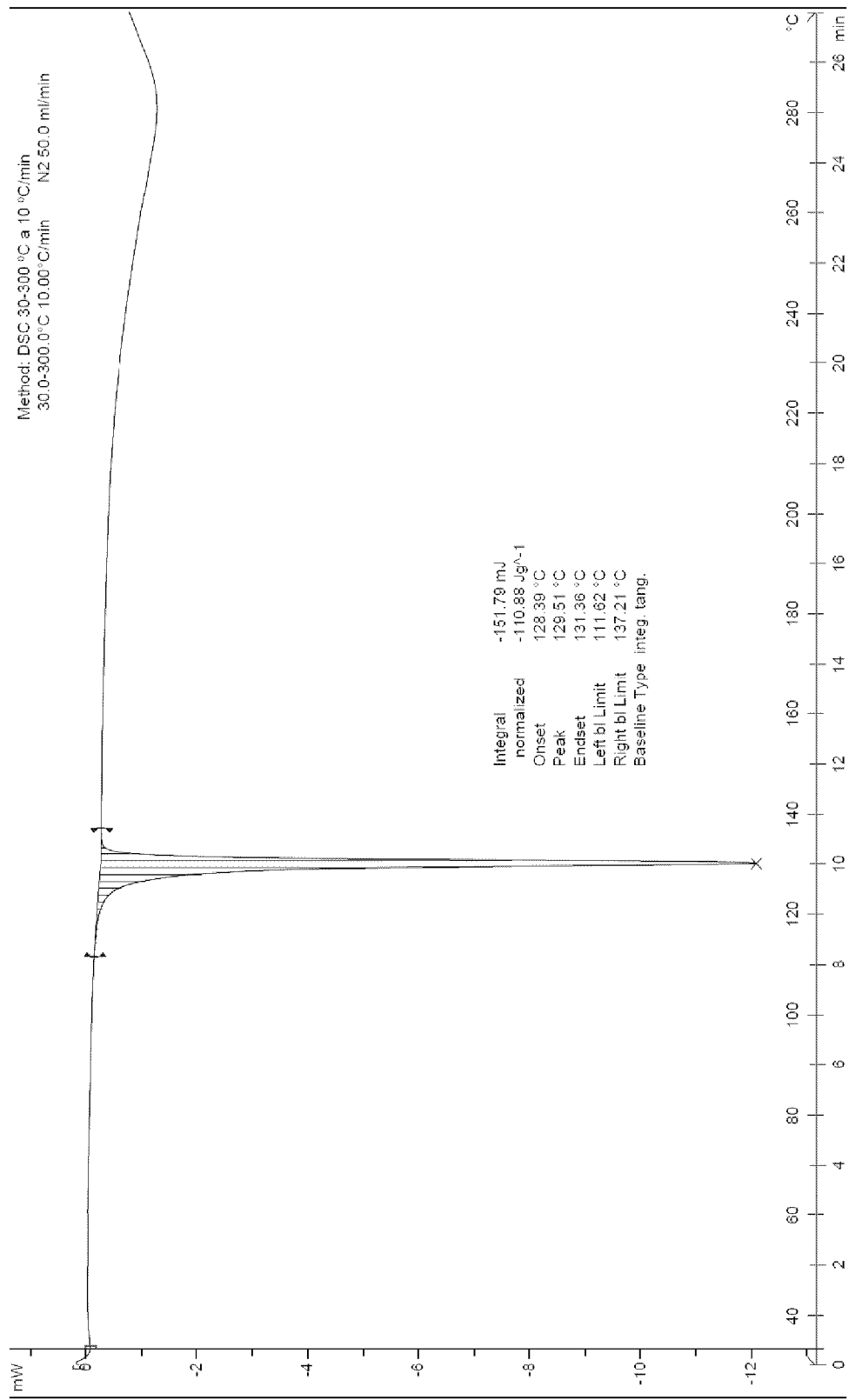

The crystalline form of (S,S)-tramadol-(R)-naproxene salt according to the present invention is characterized in that the endothermic sharp peak corresponding to the melting point has an onset at 128° C., measured by DSC analysis (10° C./min), see FIG. 10.

Figure 11:
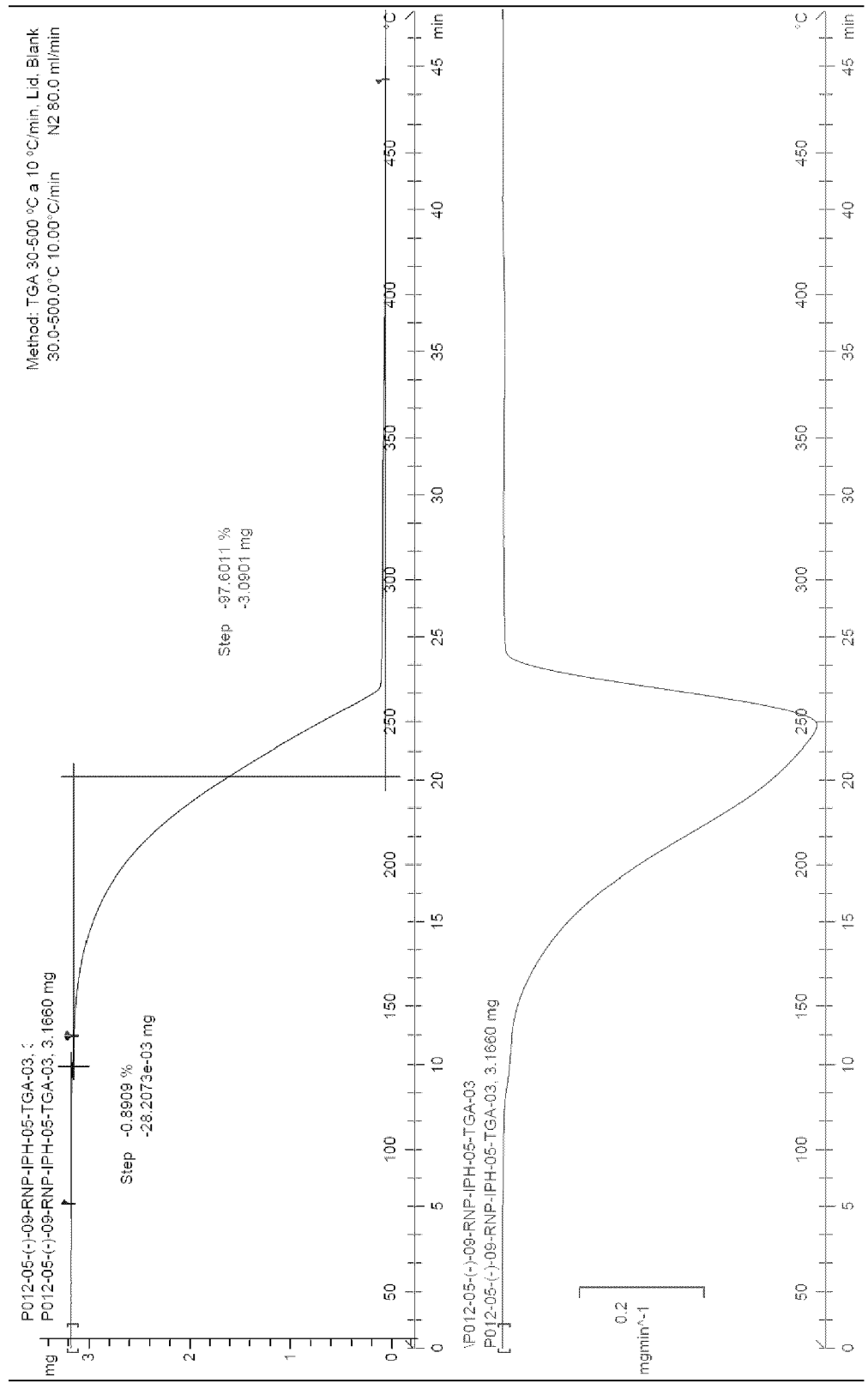

The TG analysis of the crystalline form according to the invention shows weight loss of 0.9% beginning at 120° C. followed by decomposition (see FIG. 11).

A further embodiment of the present invention is the (R,R)-tramadol-(R)-naproxene amorphous salt, in particular having a Specific rotation $[\alpha]_D^{26}=-7°$ (c=1.00, MeOH).

Still another embodiment of the invention is (S,S)-tramadol-(S)-naproxene amorphous salt, in particular having a Specific rotation $[\alpha]_D^{26}=-16°$ (c=1.00, MeOH).

In another aspect, the present invention concerns a process for the manufacture of tramadol-naproxen salts.

This process comprises the step of:
adding a solution of naproxene as a free acid in an appropriate solvent to a solution of tramadol, either as a base or as a salt, in an appropriate solvent,
heating the mixture obtained during a period of 10 minutes to 2 hours, preferably 1 hour, at a temperature comprised between 10 to 90° C.,
evaporating the solvent, and drying of the resulting product.

In the above mentioned process, one or more step can be inversed, and more particularly, in the first step, a solution of tramadol either as a base or as a salt, in an appropriate solvent may be added to a solution of naproxene as a free acid in an appropriate solvent.

If necessary in the above process, a further step of cooling to very low temperature may be added, allowing the salt obtained as an oil to give a solid. In a advantageous aspect this temperature is below –100° C., and preferably below –197° C.

The process described above preferably affords the salt according to the invention in an amorphous form.

In another embodiment the present invention concerns a process for the manufacture of (R,R)-tramadol-(S)-naproxene salt comprising the step of:
adding a solution of (S)-naproxene in an appropriate solvent to a solution of (R,R)-tramadol in an appropriate solvent,
heating the mixture obtained during a period of 0.5 to 2 hours, preferably 1 hour, at a temperature comprised between 40 to 90° C.,
evaporating the solvent, and drying of the resulting product.

Preferably, the mixture is heated at room temperature, which means 20° C. to 25° C., or at a temperature between 50 and 70° C., more particularly at 60° C.

The solvents to be used are advantageously selected among alcohols especially methanol, ethanol isopropanol, n-butanol, 2-butanol, ketones especially acetone, methyl isobutyl ketone, 3-pentanone, methyl ethyl ketone, esters more particularly ethyl acetate or isobutyl acetate, ethers especially diisopropyl ether, tetrahydrofurane, methyl t-butyl ether, hydrocarbons for example toluene, chlorobenzene, chloroform, or 1,1,1-trichloroethane and also water. In a more preferred aspect of the process for preparation of salts according to the present invention, the solvent used both for tramadol and naproxen is an alcohol, and advantageously selected among methanol and isopropanol.

A further embodiment of the present invention is a process for the manufacture o a crystalline form of (S,S)-tramadol-(R)-naproxene salt, comprising the step of:
adding a solution of (S,S)-tramadol in a solvent chosen among alcohols, ketones, esters, and ethers, to a solution of (R)-naproxene in a solvent chosen among alcohols, ketones, esters, and ethers,
heating the obtained mixture during a period of 0.5 to 2 hours, preferably 1 hour, at a temperature comprised between 40 to 90° C.,
keeping the resulting solution standing at room temperature for from 10 to 60 minutes, preferably 30 minutes, and then cooling it at a temperature comprised between 1 to 10° C. for 8 to 12 hours,
recovering the formed crystals by filtration,
washing the crystals with the solvent used, and drying.

Preferably, the process for the manufacture of a crystalline form of (R,R)-tramadol-(S)-naproxene salt according to the invention is characterized in that the volume of solvent is reduced by a factor 2 to 3 by distillation prior to cooling.

As an alternative, in the process for the manufacture of a crystalline form of (R,R)-tramadol-(S)-naproxene salt as described above, an "anti-solvent" is added to the solvent used in the first step. The anti-solvent is advantageously selected from hydrocarbons, for example pentane, hexane, or cyclohexane.

Advantageously, the process for the manufacture of a crystalline form (R,R)-tramadol-(S)-naproxene salt according to the invention is characterized in that the proportion of (S)-naproxene to (R,R)-tramadol can vary between 1 to 1 and 1 to 10, and preferably is 1 to 1.

More preferably, in the process for the manufacture of a crystalline form of (R,R)-tramadol-(S)-naproxene salt, the solvent for both (S)-naproxene and (R,R)-tramadol is an alcohol. Among the alcohols suitable for achieving the process of the invention there may be mentioned methanol, ethanol, propanol, isopropanol. More particularly the solvent used is isopropanol.

In an aspect of the invention, in the process for the manufacture of a crystalline form of (R,R)-tramadol-(S)-naproxene salt, the proportion of the solvent for both (S)-naproxene and (R,R)-tramadol is comprised between 10 and 20 ml per gram.

In another alternative of the process according to the present invention, the starting material used may be (R,R/S,S)-tramadol (racemic form of tramadol) instead of the (R,R)-enantiomer. In this case the resulting mixture of strating material and (S)-naproxen is seeded with crystalline (R,R)-tramadol-(S)-naproxen salt after cooling the heated mixture.

Thus another aspect of the invention concerns the process for the manufacture of a crystalline form of (R,R)-tramadol-(S)-naproxene salt, comprising the step of:
- adding a solution of (S)-naproxene in a solvent chosen among alcohols, ketones, esters, and ethers, to a solution of racemic-tramadol in a solvent chosen among alcohols, ketones, esters, and ethers,
- heating the mixture obtained during a period of 15 minutes to 1 hour, preferably 30 minutes, at a temperature comprised between 40 to 90° C.,
- seeding of the mixture with crystalline (R,R)-tramadol-(S)-naproxene salt,
- keeping the resulting mixture at a temperature comprised between 30 to 60° C. for another period of 15 minutes to 3 hour, preferably 30 minutes,
- cooling the mixture at a temperature comprised between 1 to 20° C., preferably 1 to 10° C., for 8 to 24 hours, preferably for 8 to 12 hours,
- recovering the formed crystals by filtration,
- washing the crystals with the solvent used, and drying.

More particularly, in the above mentioned process for the manufacture of a crystalline form of (R,R)-tramadol-(S)-naproxene salt, the proportion of (S)-naproxene to racemic-tramadol is 0.5 to 1.

In the process for the manufacture of a crystalline form of (R,R)-tramadol-(S)-naproxene salt, the solvent for both (S)-naproxene and racemic-tramadol is preferably an alcohol. Among the alcohols suitable for achieving the process of the invention there may be mentioned methanol, ethanol, propanol, isopropanol. More particularly the solvent used is isopropanol.

The above described process for obtaining (R,R)-tramadol-(S)-naproxene salt was scaled-up in order to provide a process susceptible to be used under industrial conditions. For example, when mixing the starting materials, the solution of (S)-naproxen may be pre-heated at a temperature between 60° C. and 90° C., preferably at 80° C. Advantageously in this process, the (R,R)-tramadol solution is added slowly over a period of time comprised between 10 and 30 minutes. In another aspect of this process, the solution recovered after cooling is kept under stirring for a period of time between 15 and 30 hours, in order to allow formation of the expected crystals with an improved yield.

As shown in the above mentioned process, the (R,R)-tramadol-(S)-naproxene salt according to the invention may be obtained starting from the racemic-tramadol, using (S)-naproxene.

Thus the present invention also concerns the use of (S)-naproxene for the enantiomeric resolution of racemic-tramadol.

In another embodiment the present invention concerns a process for the manufacture of (S,S)-tramadol-(R)-naproxene salt comprising the step of:
- adding a solution of (S,S)-tramadol in an appropriate solvent to a solution of (R)-naproxene in an appropriate solvent,
- heating the mixture obtained during a period of 0.5 to 2 hours, preferably 1 hour, at a temperature comprised between 40 to 90° C.,
- evaporating the solvent, and drying of the resulting product.

Preferably, the mixture is heated at room temperature, which means 20° C. to 25° C., or at a temperature between 50 and 70° C., more particularly at 60° C.

The solvents to be used are advantageously selected among alcohols especially methanol, ethanol isopropanol, n-butanol, 2-butanol, ketones especially acetone, methyl isobutyl ketone, 3-pentanone, methyl ethyl ketone, esters more particularly ethyl acetate or isobutyl acetate, ethers especially diisopropyl ether, tetrahydrofurane, methyl t-butyl ether, hydrocarbons for example toluene, chlorobenzene, chloroform, or 1,1,1-trichloroethane and also water. In a more preferred aspect of the process for preparation of salts according to the present invention, the solvent used both for tramadol and naproxen is an alcohol, and advantageously selected among methanol and isopropanol.

A further embodiment of the present invention is a process for the manufacture of a crystalline form of (S,S)-tramadol-(R)-naproxene salt, comprising the step of:
- adding a solution of (S,S)-tramadol in a solvent chosen among alcohols, ketones, esters, and ethers, to a solution of (R)-naproxene in a solvent chosen among alcohols, ketones, esters, and ethers,
- heating the obtained mixture during a period of 0.5 to 2 hours, preferably 1 hour, at a temperature comprised between 40 to 90° C.,
- keeping the resulting solution standing at room temperature for from 10 to 60 minutes, preferably 30 minutes, and then cooling it at a temperature comprised between 1 to 10° C. for 8 to 12 hours,
- recovering the formed crystals by filtration,
- washing the crystals with the solvent used, and drying.

Preferably, the process for the manufacture of a crystalline form of (S,S)-tramadol-(R)-naproxene salt according to the invention is characterized in that the volume of solvent is reduced by a factor 2 to 3 by distillation prior to cooling.

As an alternative, in the process for the manufacture of a crystalline form of (S,S)-tramadol-(R)-naproxene salt as described above, an "anti-solvent" is added to the solvent used in the first step. The anti-solvent is advantageously selected from hydrocarbons, for example pentane, hexane, or cyclohexane.

Due to the widely recognized therapeutic interest of both tramadol and naproxene and particularly of their physiologically acceptable salts and also of their association, a further object of the present invention is a medicament containing the tramadol-naproxen salt, or its crystalline form according to the invention. In one aspect of the invention, the medicament contains the (R,R)-tramadol-(S)-naproxene salt or its crystalline form. In another aspect of the invention, the medicament contains the (S,S)-tramadol-(R)-naproxene salt or its cristaline form. The present invention also concerns a medicament comprising the (R,R)-tramadol-(R)-naproxene salt, or the (S,S)-tramadol-(S)-naproxene salt.

The invention also concerns the use of a crystalline form of (R,R)-tramadol-(S)-naproxene salt as a medicament, and the use of a crystalline form of (S,S)-tramadol-(R)-naproxene salt as a medicament.

The medicament according to the present invention may be in any form suitable for the application to humans and/or animals, preferably humans including infants, children and adults and can be produced by standard procedures known to those skilled in the art. The medicament can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S. and Rhodes C. T. (Eds.) Marcel Dekker, Inc. New York 2002 y "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The composition of the medicament may vary depending on the route of administration.

Medicaments according to the present invention may also be formulated into orally administrable compositions, parentally administrable composition injected for example intramuscularly, intraperitoneally, or intravenously, containing one or more physiologically compatible carriers or excipients, in solid or liquid form.

The compositions may take any convenient form, such as tablets, pellets, granules, capsules, lozenges, aqueous or oily solutions, suspensions, emulsions, or dry powdered forms suitable for reconstitution with water or other suitable liquid medium before use, for immediate or modified or controlled release. The multiparticulate forms, such as pellets or granules, may e.g. be filled into a capsule, compressed into tablets or suspended in a suitable liquid.

Typically, the medicaments according to the present invention may contain 1-60% by weight of one or more of the salts or their crystalline form as defined herein and 40-99% by weight of one or more auxiliary substances (additives/excipients).

The compositions of the present invention may also be administered topically or via a suppository.

The daily dosage for humans and animals may vary depending on factors that have their basis in the respective species or other factors, such as age, sex, weight or degree of illness and so forth. The daily dosage for humans preferably is in the range of 10 to 2000 milligrams of active substance to be administered during one or several intakes per day. A further object of the invention is a pharmaceutical composition characterized in that it comprises an efficient amount of tramadol-naproxen salt (R,R)-tramadol-(S)-naproxene salt according to the present invention, or its crystalline form as described above, in a physiologically acceptable medium. The salt of the present invention may be advantageously chosen among (R,R)-tramadol-(S)-naproxene salt and (S,S)-tramadol-(R)-naproxene salt, as well as their crystalline forms.

A further aspect of the invention concerns the use of tramadol-naproxen salt or its crystalline form according to the invention, for the preparation of a medicament for the treatment of pain, preferably acute pain, chronic pain, neuropathic pain, hyperalgesia, allodynia or cancer pain, including diabetic neuropathy, fibromyalgia or osteoarthritis. In a preferred embodiment, the present invention concerns the use of (R,R)-tramadol-(S)-naproxene salt or its crystalline form for the preparation of a medicament for the treatment of pain, preferably acute pain, chronic pain, neuropathic pain, hyperalgesia, allodynia or cancer pain, including diabetic neuropathy, fibromyalgia or osteoarthritis. In a further preferred embodiment, the present invention concerns the use of (S,S)-tramadol-(R)-naproxene salt or its crystalline form for the preparation of a medicament for the treatment of pain, preferably acute pain, chronic pain, neuropathic pain, hyperalgesia, allodynia or cancer pain, including diabetic neuropathy, fibromyalgia or osteoarthritis.

A further aspect of the invention concerns the use of tramadol-naproxen salt or its crystalline form according to the invention, for the treatment of pain, preferably acute pain, chronic pain, neuropathic pain, hyperalgesia, allodynia or cancer pain, including diabetic neuropathy, fibromyalgia or osteoarthritis. In a preferred embodiment, the present invention concerns the use of (R,R)-tramadol-(S)-naproxene salt or its crystalline form for the treatment of pain, preferably acute pain, chronic pain, neuropathic pain, hyperalgesia, allodynia or cancer pain, including diabetic neuropathy, fibromyalgia or osteoarthritis. In a further preferred embodiment, the present invention concerns the use of (S,S)-tramadol-(R)-naproxene salt or its crystalline form for the treatment of pain, preferably acute pain, chronic pain, neuropathic pain, hyperalgesia, allodynia or cancer pain, including diabetic neuropathy, fibromyalgia or osteoarthritis.

The present invention is illustrated below with the following examples. These illustrations are given solely by way of examples and do not limit the invention.

EXAMPLE 1

Preparation of (R,R)-Tramadol-(S)-Naproxene Salt

A solution of S-naproxene (878 mg, 3.8 mmol, 1 eq) in 17 mL of isopropanol was added to a solution of (R,R)-tramadol (1.00 g, 3.8 mmol) in 10 mL of isopropanol. The mixture was heated to 60° C. for 1 hour and solvent was distilled to give the title product.

The product has been fully characterized by $^1$HNMR and by specific rotation $[\alpha]_D^{26}=+18.6°$ (c=1.00, MeOH).

Specific rotation analyses were performed in a Jasco P-1030 polarimeter, at 589 nm, using a cylindrical glass cell (10 mm i.d.×10 mm).

EXAMPLE 2

Preparation of Crystalline Form of (R,R)-Tramadol-(S)-Naproxene Salt

A solution of S-naproxene (878 mg, 3.8 mmol, 1 eq) in 17 mL of isopropanol was added to a solution of (R,R)-tramadol (1.00 g, 3.8 mmol) in 10 mL of isopropanol. The mixture was heated to 75° C. for 1 hour and solvent was distilled to a final volume of around 10 mL. The solution was left standing at room temperature, where after a few minutes a solid started to crystallize and then was kept at 3° C. overnight without stirring. The resulting mixture was filtered off, washed with isopropanol and dried under vacuum (10 mm Hg) at 40° C. for 6 hours to give the salt (R,R)-tramadol-(S)-naproxene as a white solid (1.71 g, 90%).

This product has been fully characterized by $^1$HNMR, specific rotation, FTIR, X-Ray diffraction, and melting point (see figures).

EXAMPLE 3

Scale-Up Preparation of Crystalline Form of (R,R)-Tramadol-(S)-Naproxene Salt

A solution of racemic (R,R/S,S)-tramadol (212.5 g, 0.81 mol) in 225 mL of isopropanol was added in 20 minutes to a stirred solution of (S)-naproxene (93.3 g, 0.405 mol, 0.5 eq) in 500 mL of isopropanol at 80° C.

The resulting solution was cooled to 45° C. in 1 hour and was seeded with 10-20 mg of crystalline (R,R)-tramadol-(S)-naproxene salt. Crystals started to grow at a temperature between 40 and 45° C. The suspension was cooled down to 20° C. in 3 hours, kept stirring for 22 hours and filtered off. The filtrate was washed with cold isopropanol (3×100 mL) and dried under vacuum (10 mm Hg) at 40° C. for 18 hours to give the salt (R,R)-tramadol-(S)-naproxene as a crystalline white solid (152 g, 38% yield referred to initial racemic tramadol, >99% ee).

This product has been fully characterized by $^1$HNMR, specific rotation, FTIR, X-Ray diffraction, and melting point, and is identical to the one obtained in example 2.

EXAMPLE 4

Enantiomeric Resolution of Racemic-Tramadol Using (S)-Naproxene

A solution of S-naproxene (88 mg, 0.382 mmol, 0.5 eq) in 1.5 mL of isopropanol was added to a solution of racemic-tramadol (200 mg, 0.759 mmol) in 1.5 mL of isopropanol. The solution was heated to 60° C. for 30 minutes, seeded with 1 to 5 mg of crystalline (R,R)-tramadol-(S)-naproxene salt and kept for 30 minutes at 50° C. where crystals started to grow. The mixture was slowly cooled down to 4° C. and kept at that temperature for 5 hours. The resulting suspension was filtered off, washed with isopropanol and dried under vacuum (10 mm Hg) at 40° C. overnight to give the salt (R,R)-tramadol-(S)-naproxene as a crystalline white solid (91 mg, 24%).

This product has been fully characterized by $^1$HNMR, specific rotation, FTIR, X-Ray diffraction, and melting point (see figures).

EXAMPLE 5

Preparation of (R,R)-Tramadol-(R)-Naproxene Amorphous Salt

A solution of (R)-naproxene (264 mg, 1.15 mmol) in 4 mL of methanol was added to a stirred solution of (R,R)-tramadol (300 mg, 1.15 mmol) in 2 mL of methanol. The resulting solution was stirred at room temperature for 10 minutes and the solvent was evaporated under vacuum rendering an oil. The oil was cooled to −197° C. and allowed to warm to room temperature to give the (+)-tramadol-(R)-naproxene salt as a white amorphous solid (564 mg, 100%).

$[\alpha]_D^{23}$=−7° (c=1.00, MeOH).
$^1$H NMR (400 MHz, d4-methanol) δ: 1.41-1.92 (m, 8H), 1.50 (d, J=7 Hz, 3H), 2.11 (m, 1H), 2.46 (m, 7H), 2.79 (dd, J=9 Hz, J=13 Hz, 1H), 3.73 (q, J=7 Hz, 1H), 3.80 (s, 3H), 3.89 (s, 3H), 6.80 (ddd, J=1 Hz, J=2 Hz, J=8 Hz, 1H), 7.00-7.11 (m, 3H), 7.18 (d, J=2 Hz, 1H), 7.27 (t, J=8 Hz, 1H), 7.48 (dd, J=2 Hz, J=8 Hz, 1H), 7.66-7.72 (m, 3H).
FTIR (ATR) $\upsilon_{max}$: 3338, 2933, 2857, 2835, 1705, 1632, 1603, 1582, 1483, 1458, 1389 and 1353 cm$^{-1}$.

EXAMPLE 6

Preparation of (S,S)-Tramadol-(R)-Naproxene Salt

A solution of (S,S)-tramadol (540 mg, 2.05 mmol) in 5 mL of isopropanol was added in 10 minutes to a stirred suspension of (R)-naproxene (478 mg, 2.07 mmol, 1 eq) in 4 mL of isopropanol at 60° C. After one hour solvent was distilled to give the title product.

The product has been fully characterized by $^1$HNMR and by specific rotation $[\alpha]_D^{26}$=−19° (c=1.00, MeOH).

Specific rotation analyses were performed in a Jasco P-1030 polarimeter, at 589 nm, using a cylindrical glass cell (10 mm i.d.×10 mm).

EXAMPLE 7

Preparation of Crystalline Form of (S,S)-Tramadol-(R)-Naproxene salt

A solution of (S,S)-tramadol (540 mg, 2.05 mmol) in 5 mL of isopropanol was added in 10 minutes to a stirred suspension of (R)-naproxene (478 mg, 2.07 mmol, 1 eq) in 4 mL of isopropanol at 60° C. Part of the solvent of the resulting solution was removed by evaporation and the resulting solution was cooled to room temperature. A solid crystallized, which was filtered off, washed with isopropanol and dried under vacuum (10 mm Hg) at 40° C. for 4 hours to give the (S,S)-tramadol-(R)-naproxene salt as a white solid (435 mg, 43%).

This product has been fully characterized by $^1$HNMR, specific rotation, FTIR, X-Ray diffraction, and melting point (see figures).

EXAMPLE 8

Preparation of (S,S)-Tramadol-(S)-Naproxene Amorphous Salt

A solution of (S)-naproxene (2.14 g, 9.3 mmol) in 20 mL of methanol was added in 10 minutes to a stirred solution of (S,S)-tramadol (2.45 g, 9.3 mmol) in 10 mL of methanol. The resulting solution was stirred at room temperature for 30 minutes and the solvent was evaporated under vacuum rendering a light yellow oil. The oil was cooled to −197° C. and allowed to warm to room temperature to give the (S,S)-tramadol-(S)-naproxene salt as a white solid (4.59 g, 100%).

$[\alpha]_D^{23}$=−16° (c=1.00, MeOH).
$^1$H NMR (400 MHz, d4-methanol) δ: 1.42-1.92 (m, 8H), 1.50 (d, J=7 Hz, 3H), 2.11 (m, 1H), 2.44 (dd, J=2 Hz, J=13 Hz, 1H), 2.46 (s, 6H), 2.79 (dd, J=9 Hz, J=13 Hz, 1H), 3.73 (q, J=7 Hz, 1H), 3.80 (s, 3H), 3.89 (s, 3H), 6.81 (ddd, J=1 Hz, J=2 Hz, J=8 Hz, 1H), 7.03 (d, J=8 Hz, 1H), 7.08 (dd, J=3 Hz, J=9 Hz, 2H), 7.18 (d, J=2 Hz, 1H), 7.27 (t, J=8 Hz, 1H), 7.48 (dd, J=2 Hz, J=8 Hz, 1H), 7.66-7.71 (m, 3H).
FTIR (ATR) $\upsilon_{max}$: 3336, 2932, 1705, 1632, 1603, 1581, 1504, 1482, 1459 and 1389 cm$^{-1}$.

EXAMPLE 9

Preparation of Crystalline Form of (R,R/S,S)-Tramadol-(S/R)-Naproxene Salt

Procedure 1: A solution of (R/S)-naproxene (62 mg, 0.27 mmol) in 1 mL of methanol was added to a stirred solution of (R,R/S,S)-tramadol (71 mg, 0.27 mmol) in 1 mL of methanol. The resulting solution was stirred at room temperature for 30 minutes and the solvent was evaporated under vacuum rendering an oil. The oil was dissolved in 2.5 mL of water at 70° C. and the solution was allowed to cool down to room temperature. After 2 weeks a white solid crystallized, which was filtered off and dried under vacuum (10 mm Hg) at 40° C. for 4 hours to give the (R,R/S,S)-tramadol-(R/S)-naproxene salt.

The same salt was obtained crystallizing in dichloromethane, toluene, methyl isobutyl ketone, 3-pentanone, 1,1,1-trichloroethane.

Procedure 2: A solution of (R/S)-naproxene (190 mg, 0.83 mmol) in 1 mL of methanol was added to a stirred solution of (R,R/S,S)-tramadol (215 mg, 0.82 mmol) in 1 mL of methanol. The resulting solution was stirred at room temperature for 30 minutes and the solvent was evaporated under vacuum rendering an oil. The oil was dissolved in 0.6 mL of dioxane at 50° C. and n-hexane was added until turbidity appeared. The solution was allowed to cool down to room temperature. After 24 hours a white solid crystallized, which was filtered off and dried under vacuum (10 mm Hg) at 40° C. for 4 hours to give the (R,R/S,S)-tramadol-(R/S)-naproxene salt (278 mg, 69%).

Characterization of the (R,R/S,S)-Tramadol-(R/S)-Naproxene Salt.

The obtained solid is formed by a mixture of the (R,R)-tramadol-(S)-naproxene salt and the (S,S)-tramadol-(R)-naproxene salt. Both salts crystallize simultaneously but in different crystalline cells forming a conglomerate. Thus, the PXRD pattern shows the same reflections as the enantiomeric pure salts separately.

$^1$H NMR (400 MHz, d4-methanol) δ: 1.41-1.92 (m, 8H), 1.50 (d, J=7 Hz, 3H), 2.12 (m, 1H), 2.41-2.50 (m, 7H), 2.79 (dd, J=9 Hz, J=13 Hz, 1H), 3.74 (q, J=7 Hz, 1H), 3.80 (s, 3H), 3.89 (s, 3H), 6.81 (ddd, J=1 Hz, J=3 Hz, J=8 Hz, 1H), 7.03 (d, J=8 Hz, 1H), 7.08 (dd, J=2 Hz, J=9 Hz, 2H), 7.18 (d, J=2 Hz, 1H), 7.27 (t, J=8 Hz, 1H), 7.48 (dd, J=2 Hz, J=8 Hz, 1H), 7.66-7.72 (m, 3H).

FTIR (ATR) $\upsilon_{max}$: 3207, 2935, 2287, 1602, 1579, 1504, 1483, 1454, 1386 and 1351 cm$^{-1}$.

DSC (10° C./min): Endothermic peak corresponding to the melting point with an onset at 97° C.

TGA (10° C./min): Weight loss over 120° C. due to decomposition.

EXAMPLE 10

Determination of the Hygroscopicity of the Crystalline Salts According to the Invention The objective was to measure the hygroscopicity of the salts of the present invention, and comparing it with the one of the known salt of each counter part of the salts. The increasing of the weight will be measured in order to evaluate the incorporation of water in the samples, together with the Karl Fischer factor.

According to "Technical guide for the elaboration of monographs" special issue PharmaEuropa, 3$^{rd}$ ed., December 1999, the hygroscopicity is defined based on the augmentation of weight after 24 hours of exposition to 80% of relative humidity at 25° C. The scale is the following:

| % incorporation of water | |
|---|---|
| Δ < 0.2% | No hygroscopic |
| 0.2% < Δ < 2% | Slightly hygroscopic |
| 2% < Δ < 15% | Hygroscopic |
| 15% < Δ | Very hygroscopic |
| Dissolved in water | Deliquescent |

Methods:
Preparation of the Humidity chamber: A supersaturated solution of sodium nitrite (45 g/50 ml) is prepared and introduced in a humidification chamber (samplaterecord). The chamber is maintained at a temperature of 25±2° C. during 24 hours before use, and humidity is controlled each day. Conditioned in that way the chamber has 64% of relative humidity at a temperature of 25±2° C.

Three samples are prepared:
Sample 1: 200 mg of crystalline salt of example 2,
Sample 2: 121.5 mg of tramadol hydrochloride,
Sample 3. 102.2 mg of sodium naproxen.
The samples are introduced in the conditioned humidity chamber, and the weight is controlled after 24 hours, 48 hours, and 6 days, till an equilibrium is reached (2 successive control with a variation of weight less than 0.2 mg).

The Karl Fischer is also determined (using a Methrom 756 KF) at the beginning and at the end of the study.

Results:
The variation of the weight is controlled and the following percentage is calculated:

$$\Delta\% \text{ weigth} = (P_n - P_1)/P_1 \times 100$$

wherein: $P_1$ is the initial weight, $P_n$ is the weight measured for the sample.

The results are summarized in the following table 3:

TABLE 3

% of variation of the weight and Karl Fischer value

| Sample | KF (t = 0) | Δ % weigth 24 h | Δ % weigth 48 h | Δ % weigth 6 days | KF (t = 6 days) |
|---|---|---|---|---|---|
| Sample 1 | 0.34 | 0 | 0 | 0 | 0.2 |
| Sample 2 | 0.45 | 0.19 | 0.26 | 0.18 | 0.23 |
| Sample 3 | 1.04 | 14.39 | 14.39 | 14.3 | 12.65 |

According to the above mentioned scale, whereas the sodium naproxen is hygroscopic, and the tramadol hydrochloride is slightly hygroscopic, the crystalline salt of example 2 is not hygroscopic, and also exhibit a lower KF, which means it incorporates much less water, with slightly no variation over the time.

Further an observation confirmed that the crystalline salt of example 2 (sample 1) remains a powder, whereas in the two other samples the powder is agglomerating in the course of the experiment.

EXAMPLE 11

Pharmacological Activity of the Salt of the Invention

The effect of the salts of the present invention on pain is measured in a model of visceral pain well known in the art: the TNBS-induced colonic hypersensitivity. In this model, the injection of trinitrobenzene sulfonic acid (TNBS) into the proximal colon provoke chronic colonic hypersensitivity, measured in conscious rats by a decreased pain threshold in response to colonic distension.

Methods
The animals are Male Sprague-Dawley rats (360-400 g, France). They were housed in a temperature (19.5° C. 24.5° C.) and relative humidity (45%-65%) controlled room with a 12 h—light/dark cycle, with ad libitum access to standard pelleted laboratory chow and water throughout the study.

Animals were housed 4 per cage and an acclimation period (1 week) was observed before any testing. Each rat was identified on the tail.

The study was performed according to the guidelines of the Committee for Research and Ethical Issue of the I.A.S.P. (1983).

The experiment was conducted with two samples:
Example 2: the crystalline salt of (R,R)-tramadol-(S)-naproxen, and
Combo-02: which is the molar combination of two drugs in a ratio (1:1): (R,R) tramadol,HCl and (S)-naproxen,Na,
and using two controls:
The Vehicle: 1% Methyl cellulose aqueous solution (w/v) and,
The reagent: TNBS (Fluka, Switzerland).

Experimental Procedure

Intracolonic Administration of TNBS

Fasted (24 hours) animals were undergoing surgery for administration of TNBS (50 mg/kg) into the proximal part of the colon.

After surgery, the animals were kept in individual cages in a regulated environment, and fed ad libitum until the day of the test (7 days later).

Five determinations of colonic threshold were performed before treatment, and at t=0, 20, 45, 90 and 120 min after treatment.

Colonic Distension

Day 7 after TNBS injection: Compounds were administered and the colonic hypersensitivity due to TNBS-induced colonic inflammation was measured before the treatment, and at t=20, 45, 90 and 120 min after treatment. The pain threshold corresponds to the pressure that produced the first abdominal contraction. To determine the colonic threshold, increasing colonic pressure was applied on the same animal with a step of 5 mm Hg; 30 sec (cut-off 75 mm Hg).

Distribution of the treatment groups was as follows
- A <<naive>> group composed of animals not undergoing surgery on D-7.
- A <<TNBS>> group composed of animals undergoing surgery and receiving TNBS on D-7 and treated with the treatment vehicle (1% methyl cellulose aqueous solution) before measurement of the colonic distention threshold.
- A <<Treated>> group composed of animals undergoing surgery and receiving TNBS on D-7 and treated with the treatments before measurement of the colonic distention threshold. Treatments were: Example 2 and Combo-02. Compounds were administered at 5 mg/kg. Doses were expressed in terms of free active substance (free base). Compounds were orally given (2.5 ml/kg) in 1% methyl cellulose aqueous solution as a vehicle.

Data Presentation and Statistical Analyses

For the final results (anti-hypersensitive effect), calculations of the arithmetic mean and the standard error mean (SEM) of the distention threshold were conducted. The 95% confidence intervals of each of the arithmetic means were also calculated.

Statistical significance between the treated groups and the vehicle-treated group was determined by a two-way repeated measures ANOVA followed, when F-value is significant, by an appropriate post-hoc comparison (Bonferroni's test) using SigmaStat software.

Results: The results are shown on FIG. 12, and clearly demonstrate the superior effect of the salt of the invention over the corresponding combination of the two corresponding species. Even more the treated animals with the salt of example 2 is nearly recovering the same level of colonic threshold than the naive animal. On the other hand animals treated with the combo-02 present a much lower colonic threshold.

FIG. 1: FT-IR Spectrum of Crystalline Form of (R,R)-Tramadol-(S)-Naproxene Salt.

The FTIR spectra were recorded using a Bruker Tensor 27, equipped with a MKII golden gate single reflection ATR system, a mid-infrared source as the excitation source and a DTGS detector. The spectra were acquired in 32 scans at a resolution of 4 cm$^{-1}$.

Figure 2:
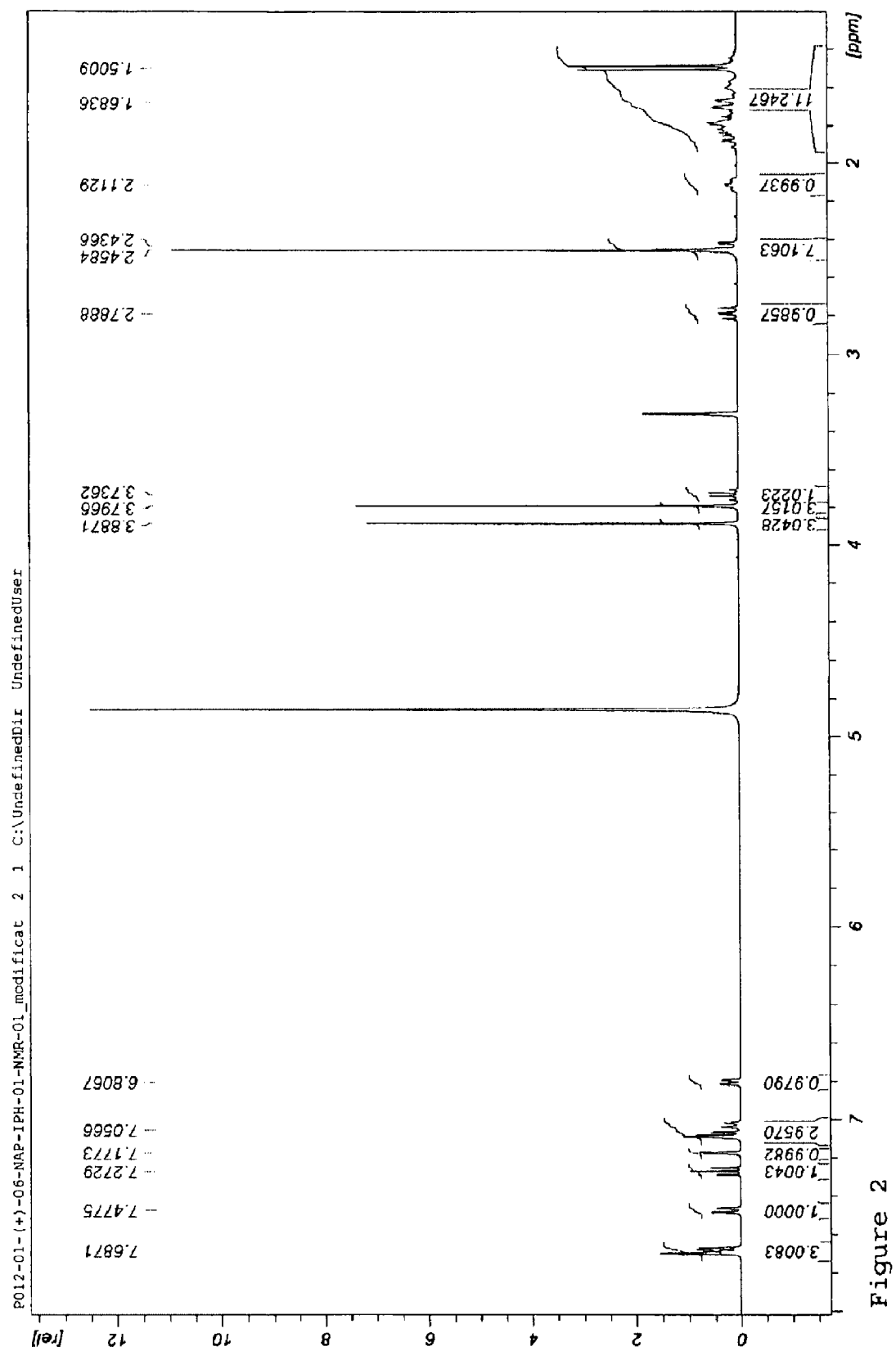

FIG. 2: $^1$H-NMR Spectrum of Crystalline Form of (R,R)-Tramadol-(S)-Naproxene Salt.

Proton nuclear magnetic resonance analyses were recorded in deuterated methanol (MeOH-d4) in a Bruker Avance 400 Ultrashield NMR spectrometer, equipped with a z-gradient 5 mm BBO (Broadband Observe) probe. Spectra were acquired solving 2-10 mg of sample in 0.6 mL of deuterated solvent.

FIG. 3: Powder X-Ray Diffraction Pattern of Crystalline Form of (R,R)-Tramadol-(S)-Naproxene Salt (PXRD).

Approximately 20 mg of the samples were prepared in standard sample holders using two foils of polyacetate. Powder diffraction patterns were acquired on a D8 Advance Series 2 Theta/Theta powder diffraction system using $Cu_{K\alpha}$-radiation in transmission geometry. The system is equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0.

FIG. 4: Structure of the Crystalline Form of (R,R)-Tramadol-(S)-Naproxene Salt Obtained by SCXRD Analysis.

The measured crystal was selected using a Zeiss stereomicroscope using polarized light and prepared under inert conditions immersed in perfluoropolyether as protecting oil for manipulation. Crystal structure determination was carried out using a Bruker-Nonius diffractometer equipped with a APPEX 2 4K CCD area detector, a FR591 rotating anode with $Mo_{K\alpha}$ radiation, Montel mirrors as monochromator and a Kryoflex low temperature device (T=100 K). Fullsphere data collection omega and phi scans. Programs used: Data collection Apex2 V. 1.0-22 (Bruker-Nonius 2004), data reduction Saint+Version 6.22 (Bruker-Nonius 2001) and absorption correction SADABS V. 2.10 (2003). Crystal structure solution was achieved using direct methods as implemented in SHELXTL Version 6.10 (Sheldrick, Universität Göttingen (Germany), 2000) and visualized using XP program. Missing atoms were subsequently located from difference Fourier synthesis and added to the atom list. Least-squares refinement on $F_0^2$ using all measured intensities was carried out using the program SHELXTL Version 6.10 (Sheldrick, Universität Göttingen (Germany), 2000). All non hydrogen atoms were refined including anisotropic displacement parameters FIG. 5: DSC Analysis of Crystalline Form of (R,R)-Tramadol-(S)-Naproxene Salt.

DSC analyses were recorded in a Mettler Toledo DSC822e. Samples of 1-2 mg were weighted into 40 µL aluminium crucibles with a pinhole lid, and were heated, under nitrogen (50 mL/min), at 10° C./min from 30 to 300° C.

FIG. 6: TG Analysis of Crystalline Form of (R,R)-Tramadol-(S)-Naproxene Salt.

Thermogravimetric analyses were recorded in a Mettler Toledo SDTA851e. Samples of 3-4 mg were weighted into 40 µL aluminium crucibles with a pinhole lid, and heated at 10° C./min from 30 to 500° C., under nitrogen (80 mL/min).

FIG. 7: FT-IR Spectrum of Crystalline Form of (S,S)-Tramadol-(R)-Naproxene Salt.

The FTIR spectra were recorded using a Bruker Tensor 27, equipped with a MKII golden gate single reflection ATR system, a mid-infrared source as the excitation source and a DTGS detector. The spectra were acquired in 32 scans at a resolution of 4 cm$^{-1}$.

Figure 8:
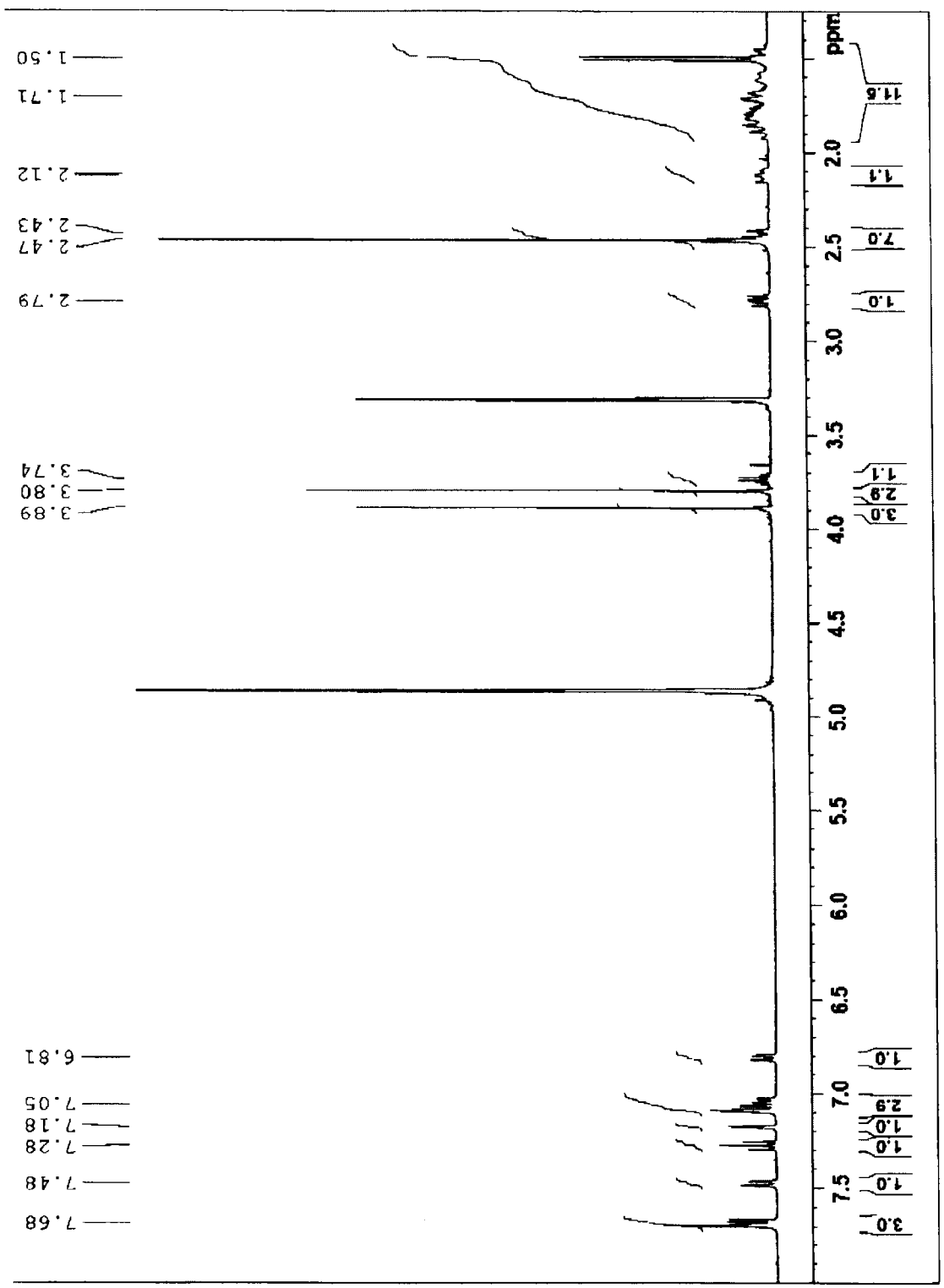

FIG. 8: $^1$H-NMR Spectrum of Crystalline Form of (S,S)-Tramadol-(R)-Naproxene Salt.

Proton nuclear magnetic resonance analyses were recorded in deuterated methanol (MeOH-d4) in a Bruker Avance 400 Ultrashield NMR spectrometer, equipped with a z-gradient 5 mm BBO (Broadband Observe) probe. Spectra were acquired solving 2-10 mg of sample in 0.6 mL of deuterated solvent.

FIG. 9: Powder X-Ray Diffraction Pattern of Crystalline Form of (S,S)-Tramadol-(R)-Naproxene Salt (PXRD).

Approximately 20 mg of the samples were prepared in standard sample holders using two foils of polyacetate. Powder diffraction patterns were acquired on a D8 Advance Series 2 Theta/Theta powder diffraction system using $Cv_{K\alpha}$ radiation in transmission geometry. The system is equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0.

FIG. 10: DSC Analysis of Crystalline Form of (S,S)-Tramadol-(R)-Naproxene Salt.

DSC analyses were recorded in a Mettler Toledo DSC822e. Samples of 1-2 mg were weighted into 40 μL aluminium crucibles with a pinhole lid, and were heated, under nitrogen (50 mL/min), at 10° C./min from 30 to 300° C.

FIG. 11: TG Analysis of Crystalline Form of (S,S)-Tramadol-(R)-Naproxene Salt.

Thermogravimetric analyses were recorded in a Mettler Toledo SDTA851e. Samples of 3-4 mg were weighted into 40 μL aluminium crucibles with a pinhole lid, and heated at 10° C./min from 30 to 500° C., under nitrogen (80 mL/min).

Figure 12:
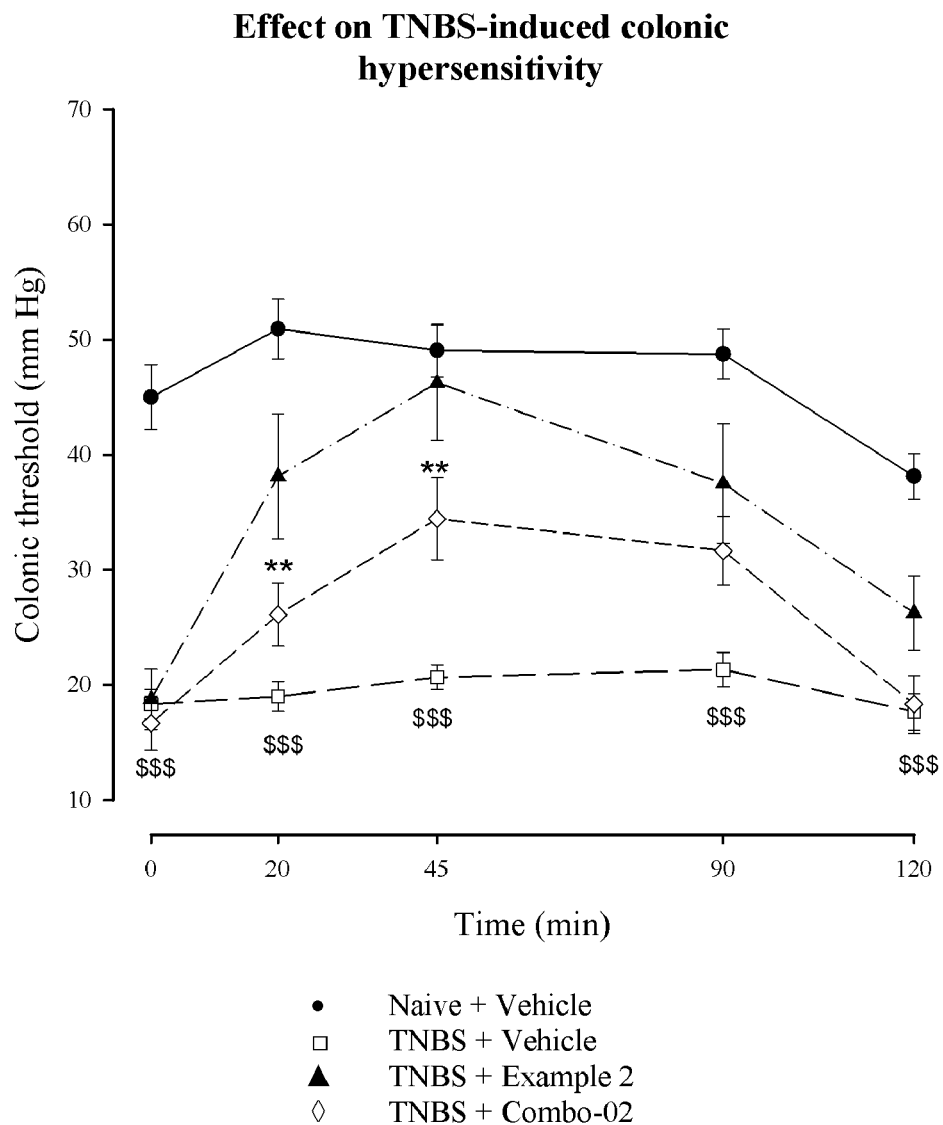

FIG. 12: Effect of the Crystalline Form of (R,R)-Tramadol-(S)-Naproxene Salt of Example 2 on TNBS-Induced Colonic Hypersensitivity.

Kinetic of antihypersensitive effect of example 2 and combo-02 on TNBS-induced hypersensitivity. Combo-02 was prepared as a molar combination (ratio 1:1) of (R,R)-Tramadol plus (S)-naproxen. The points and the vertical lines that cross them represent the mean±S.E.M. *: $p<0.05$; **: $p<0.01$ Example 2 vs Combo-02 $$$: $p<0.001$ TNBS vs Naive group (Bonferroni's test).

The invention claimed is:

1. A crystalline form of (R,R)-tramadol-(S)-naproxen salt, characterized in that it shows a X-Ray powder diffraction spectrum with peaks expressed in d-Value in Å at 10.06097, 8.11136, 7.89107, 6.71252, 6.36201, 5.96828, 5.44203, 5.37442, 5.25780, 5.02147, 4.95258, 4.85099, 4.83229, 4.67202, 4.63922, 4.51720, 4.27993, 4.14654, 4.05593, 3.93014, 3.90666, 3.84436, 3.73331, 3.58933, 3.54954, 3.37803, 3.35447, 3.29816, 3.26483, 3.23509, 3.17870, and 3.06515.

2. A crystalline form of (R,R)-tramadol-(S)-naproxen salt, characterized in that it crystallizes as a monoclinic cell with the following dimensions:
a=10.073(5)Å
b=12.487(6)Å
c=10.630(6)Å
β angle of 98.91(3)°.

3. A crystalline form of (R,R)-tramadol-(S)-naproxen salt, characterized in that the endothermic sharp peak corresponding to the melting point has an onset at 129° C.

4. A crystalline form of (R,R)-tramadol-(S)-naproxen salt, according to claim 3, characterized in that the specific rotation $[\alpha]_D^{26}$ is +18.6°.

* * * * *